(12) United States Patent
Ilongo

(10) Patent No.: US 12,145,181 B2
(45) Date of Patent: Nov. 19, 2024

(54) CLEANING SYSTEM FOR DIAPHRAGM PUMP

(71) Applicant: Abiomed, Inc., Danvers, MA (US)

(72) Inventor: Emmanuel N. Ilongo, Manchester-by-the-Sea, MA (US)

(73) Assignee: Abiomed, Inc., Danvers, MA (US)

( * ) Notice: Subject to any disclaimer, the term of this patent is extended or adjusted under 35 U.S.C. 154(b) by 927 days.

(21) Appl. No.: 17/060,329

(22) Filed: Oct. 1, 2020

(65) Prior Publication Data

US 2021/0101189 A1 Apr. 8, 2021

Related U.S. Application Data

(60) Provisional application No. 62/910,078, filed on Oct. 3, 2019.

(51) Int. Cl.
*B08B 9/032* (2006.01)
*A61M 60/268* (2021.01)
(Continued)

(52) U.S. Cl.
CPC ......... *B08B 9/0328* (2013.01); *A61M 60/268* (2021.01); *B08B 9/0325* (2013.01);
(Continued)

(58) Field of Classification Search
CPC ....... B08B 9/027; B08B 9/032; B08B 9/0321; B08B 9/0323; B08B 9/0325;
(Continued)

(56) References Cited

U.S. PATENT DOCUMENTS 1,552,998 A * 9/1925 Menge ............... F01M 11/0458
134/107
3,385,735 A * 5/1968 Brabrand ............... B01D 37/00
134/28
(Continued)

FOREIGN PATENT DOCUMENTS

DE 102011117060 A1 5/2013
GB 1383646 A 2/1974
(Continued)

OTHER PUBLICATIONS

Machine Translation of Voelker, DE 102011117060 A1, May 2013. (Year: 2013).*
(Continued)

*Primary Examiner* — David G Cormier
(74) *Attorney, Agent, or Firm* — Botos Churchill IP Law LLP

(57) ABSTRACT

Apparatus and methods for cleaning a single-port fluidic device, such as a single-port, diaphragm-based cardiac pump, with a continuous stream of fresh cleaning fluid, while simultaneously draining soiled fluid, via a single input-output port of the fluidic device. A first coupler releasably mates with the input-output port. The first coupler includes an injector nozzle and a return port. The injector nozzle is oriented to direct a stream of pressurized cleaning fluid toward an interior chamber of the single-port fluidic device. The return port simultaneously removes soiled cleaning fluid from the interior chamber. A circulation pump delivers the pressurized cleaning fluid from a tank to the injector nozzle, and returns soiled cleaning fluid from the return port to the tank, via a cleaning fluid circulation circuit. Optionally, the diaphragm may be alternately driven between two positions, to agitate the cleaning fluid within the interior chamber, thereby enhancing cleaning efficiency.

16 Claims, 8 Drawing Sheets

(51) Int. Cl.
    *B08B 13/00*      (2006.01)
    *F04B 43/02*      (2006.01)
    *A61M 60/148*      (2021.01)

(52) U.S. Cl.
    CPC .............. *B08B 13/00* (2013.01); *F04B 43/02* (2013.01); *A61M 60/148* (2021.01); *A61M 2209/10* (2013.01); *B08B 2209/032* (2013.01)

(58) Field of Classification Search
    CPC ..... B08B 9/0326; B08B 9/0328; B08B 9/035; B08B 2209/032; A61M 2209/10; F28G 9/00
    See application file for complete search history.

(56) References Cited

U.S. PATENT DOCUMENTS

| | | | |
|---|---|---|---|
| 5,589,070 | A | 12/1996 | Maltais et al. |
| 5,603,775 | A * | 2/1997 | Sjoberg ................... D21F 1/325 15/345 |
| 8,157,925 | B1 | 4/2012 | Templin |
| 2001/0015216 | A1 | 8/2001 | Reicks |
| 2001/0032494 | A1* | 10/2001 | Greszler ................ A61B 1/125 73/40 |
| 2014/0238110 | A1* | 8/2014 | Williams ............ G01M 3/2846 73/40 |
| 2017/0173228 | A1 | 6/2017 | Ehlert |
| 2017/0332892 | A1* | 11/2017 | Yang ........................ B08B 3/10 |

FOREIGN PATENT DOCUMENTS

| | | |
|---|---|---|
| JP | 2003027411 A | 1/2003 |
| JP | 2015183722 A | 10/2015 |

OTHER PUBLICATIONS

International Search Report and Written Opinion for Application No. PCTUS2020053736 dated Feb. 23, 2021.

Article 94(3) Communication dated Sep. 5, 2024 issued in EP Application No. 20799871.7-1017.

* cited by examiner

CLEANING SYSTEM FOR DIAPHRAGM PUMP

CROSS-REFERENCE TO RELATED APPLICATIONS

This application claims the benefit of U.S. Provisional Patent Application No. 62/910,078, filed 3 Oct. 2019, titled "Cleaning System for Diaphragm Pump," the entire contents of which are hereby incorporated by reference herein, for all purposes.

BACKGROUND

Technical Field

The present invention relates to cleaning systems for pumps and, more particularly, to cleaning systems for single-port diaphragm pumps.

Related Art

Heart pumps and other medical devices that are implanted in, or otherwise connected to, patients must be clean, and sometimes sterile, before use. Pumps and other "plumbing" apparatus used to process foods, drugs and other products have similar requirements. Multi-ported fluidic devices are relatively easy to clean, for example by flushing. A continuous stream of fresh cleaning fluid may be introduced via one port, while simultaneously soiled fluid may be drained via another port.

However, single-port fluidic devices, such as the Symphony cardiac assist device introduced by Abiomed, Inc., Danvers, MA, have been notoriously difficult to clean. Each such device has only one port to its interior. Consequently, the pump interior cannot simply be flushed by continuously introducing cleaning fluid into a first port and simultaneously extracting soiled cleaning fluid via a second port. Conventional cleaning apparatus and protocols cannot continuously and simultaneously replace soiled cleaning fluid with fresh cleaning fluid.

Instead, a single-port fluidic device must be either dismantled for cleaning, or the device can be alternatingly filled and emptied via the single port. For example, a single-port fluidic device may be cleaned by introducing cleaning fluid through the single port, shaking the device, expelling used cleaning fluid and then repeating these steps. However, tests have shown that this method does not adequately clean devices intended for critical uses, such as pumping human blood. For example, alternatingly filling and emptying a single-port fluidic device necessarily contaminates the device with the soiled fluid that was most recently in the device. Both methods are time consuming and often produce less than satisfactory results.

SUMMARY OF EMBODIMENTS

An embodiment of the present invention provides a cleaning system for a diaphragm pump. The diaphragm pump includes a housing, a diaphragm disposed within the housing and an input-output port. The diaphragm and at least a portion of the housing collectively defining a pump chamber interior. The input-output port is in fluid communication with the pump chamber interior.

The cleaning system includes a tank configured to store a cleaning fluid.

A first coupler is configured to releasable mate, and thereby create a fluid-tight connection, with the input-output port. The first coupler includes an injector nozzle. The injector nozzle has an input end and an output end. The injector nozzle is configured such that, while the first coupler is mated with the input-output port, the injector nozzle is in fluid communication with, and oriented to direct a fluid stream toward, the pump chamber interior.

The first coupler also includes a return port. The return port is proximate, and distinct from, the output end of the injector nozzle. The return port is configured, such that while the first coupler is mated with the input-output port, the return port is in fluid communication with the pump chamber interior.

The injector nozzle is configured to direct the stream into the pump chamber interior simultaneous with the return port draining the pump chamber interior.

The cleaning system also includes a circulation pump. The circulation pump has an input and an output. A cleaning fluid circulation circuit is in fluid communication with the tank, the input and the output of the circulation pump, the input end of the injector nozzle and the output port. The cleaning fluid circulation circuit is configured to deliver pressurized cleaning fluid from the tank to the injector nozzle and to return used cleaning fluid from the output port to the tank.

Optionally, in any embodiment, the cleaning system may further include a first two-way valve in the cleaning fluid circulation circuit. The first two-way valve has an input, a first output and a second output. The first two-way valve is user settable to either of two states. The first two-way valve is configured to place the input into fluid communication with either the first output or the second output depending on the state of the first two-way valve. The input is coupled to the output of the circulation pump. The first output is coupled to the input end of the injector nozzle, and the second output is coupled to the tank thereby bypassing the first coupler.

Optionally, in any embodiment that includes the first two-way valve, the cleaning system may further include a purge port and a second two-way valve in the cleaning fluid circulation circuit. The second two-way valve has an input, a first output and a second output. The second two-way valve is user settable to either of two states. The second two-way valve is configured to place the input of the second two-way valve into fluid communication with either the first output of the second two-way valve or the second output of the second two-way valve depending on the state of the second two-way valve. The input of the second two-way valve is coupled to the output of the circulation pump. The first output of the second two-way valve is coupled to the input of the first two-way valve, and the second output of the second two-way valve is coupled to the purge port.

Optionally, in any embodiment, the circulation pump may be pneumatically driven. Optionally, in any embodiment, the circulation pump may be electrically driven.

Optionally, in any embodiment usable with a diaphragm pump that includes a pneumatic diaphragm activation port, the cleaning system may further include a second coupler. The second coupler may be configured to releasably mate with, and thereby create a gas-tight connection with, the pneumatic diaphragm activation port. The cleaning system may also include a source of gas. The source of gas may be configured to supply the gas to the second coupler at a pressure that alternates, at a frequency between about 0.1 Hz and about 10 Hz. The source of gas may be configured to supply the gas to the second coupler between a first pressure and a second pressure. The second pressure may be greater than the first pressure by at least about 1.45 PSI (9,997 Pa).

Optionally, in any embodiment usable with a diaphragm pump that includes a pneumatic diaphragm activation port, the source of gas may include a pneumatically driven Venturi configured to supply gas at about 2-3 inHg (6,772.78-10,159.2 Pa).

Optionally, in any embodiment usable with a diaphragm pump that includes a pneumatic diaphragm activation port, the first pressure may be less than ambient atmospheric pressure, and the second pressure may be greater than ambient atmospheric pressure.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Embodiments of the present invention provide apparatus and methods for cleaning single-port fluidic devices, such as the aforementioned Symphony cardiac assist device, with a continuous stream of fresh cleaning fluid, while simultaneously draining soiled fluid, via a single port. Although usable with other single-port fluidic devices, and even multi-port fluidic devices, embodiments of the present invention are described herein in the context of cleaning a Symphony single-port cardiac assist device.

Figure 1:
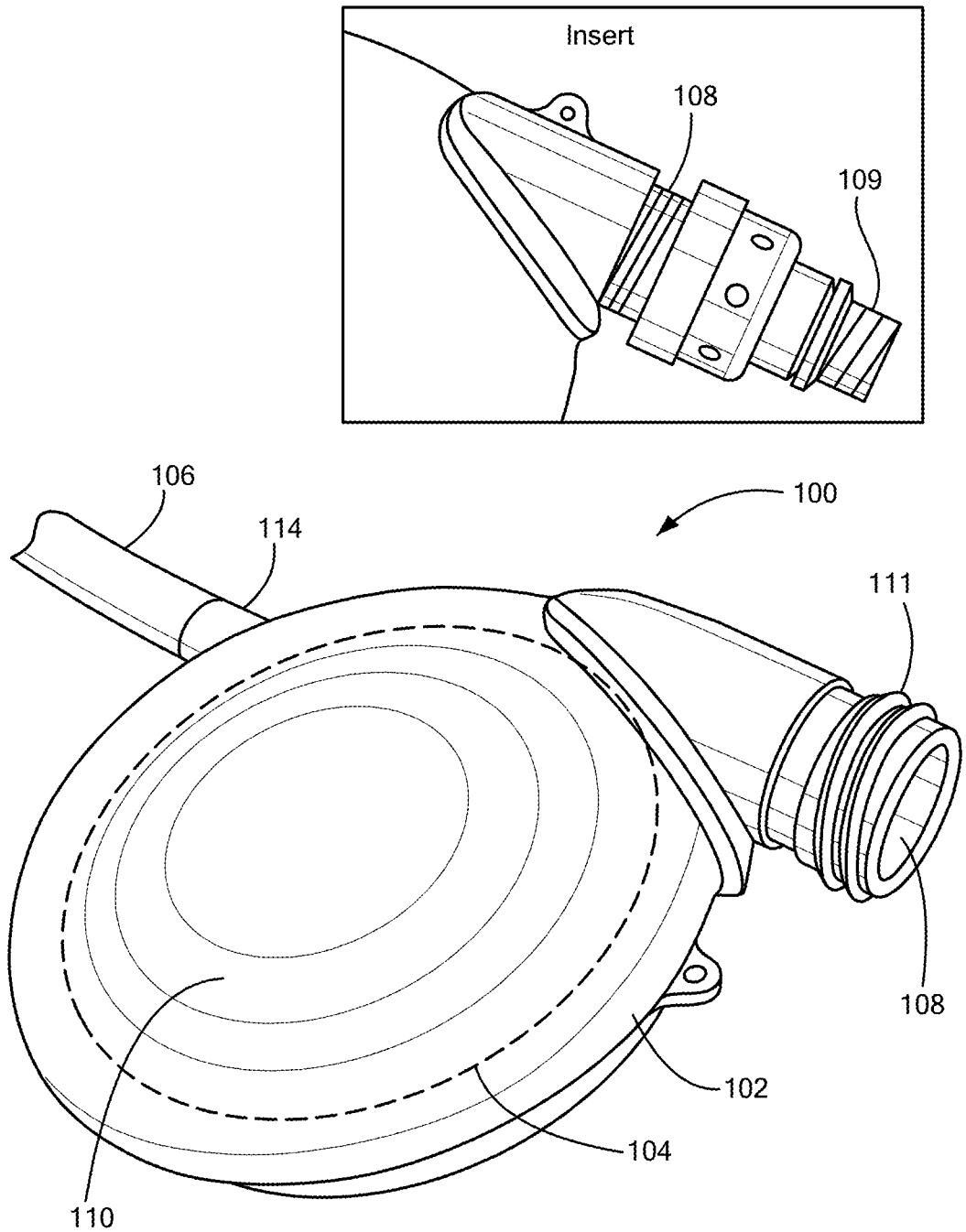
FIGS. 1 and 2 are respective perspective and side views of an exemplary prior art single-port diaphragm pump that may be cleaned using embodiments of the present invention.
Figure 2:
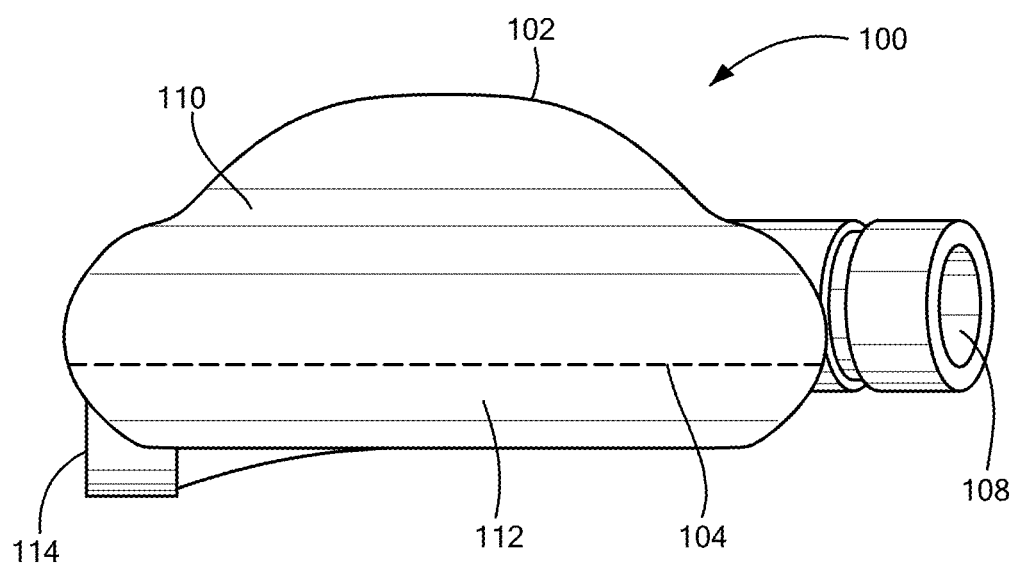

FIGS. 1 and 2 are respective perspective and side views of the Symphony cardiac assist device 100. The Symphony device 100 serves as an exemplary single-port diaphragm pump 100 that may be cleaned using embodiments of the present invention. The Symphony cardiac assist device 100 is also referred to herein as a single-port diaphragm pump 100.

The Symphony device 100 is a valveless counter-pulsation cardiac assist device designed for superficial implantation in a patient's "pacemaker pocket." The Symphony device 100 includes a housing 102 and a pneumatically-driven sac that includes a flexible diaphragm 104 (not visible, but shown in phantom). The diaphragm 104 is operated by a small wearable pneumatic driver (not shown) connected to the sac by a percutaneous air line 106. The Symphony device 100 has a single input-output port 108 that is connected to the patient's subclavian artery via a conduit. An insert of FIG. 1 shows a portion of the Symphony device 100 with a conduit 109 coupled to the single input-output port 108.

The pneumatic driver is synchronized to the patient's heartbeat, based on electrocardiogram (ECG) signals from the patient's heart. The Symphony device 100 fills with blood from the artery during the heart's natural expansion, lowering the heart muscles' workload. The Symphony device 100 ejects blood back into the artery during the heart's natural contraction, increasing blood flow throughout the body, thereby improving the patient's overall health.

The diaphragm 104 is disposed within the housing 102. Collectively, the diaphragm 104 and at least a portion of the housing 102 define a fluid-tight interior volume (a pump chamber interior) 110 that is in fluid communication with the single input-output port 108. One side of the diaphragm 104 faces the interior volume 110. The single input-output port 108 is mechanically attached to the housing 102 and may include a threaded or other type of releasable-mating feature 111 configured to releasably mate with the conduit 109.

In use, the input-output port 108 is coupled in fluid communication with the patient's cardiovascular (blood circulatory) system via the conduit 109. No other port is in fluid communication with the interior volume 110, hence the device is designated a "single-port" fluidic device.

The other side of the diaphragm 104 and at least a portion of the housing 102 define a second interior volume 112. A pneumatic actuation port 114 is in fluid communication with the second interior volume 112. In use, the pneumatic actuation port 114 is connected, by the air line 106, in fluid communication with the small wearable pneumatic driver (not shown), or another suitable supply of alternating pressure and suction, which reciprocates the diaphragm 104. The reciprocating diaphragm 104 pumps fluid, such as blood, alternatingly in and out of the first interior chamber 110, via the input-output port 108.

Figure 3:
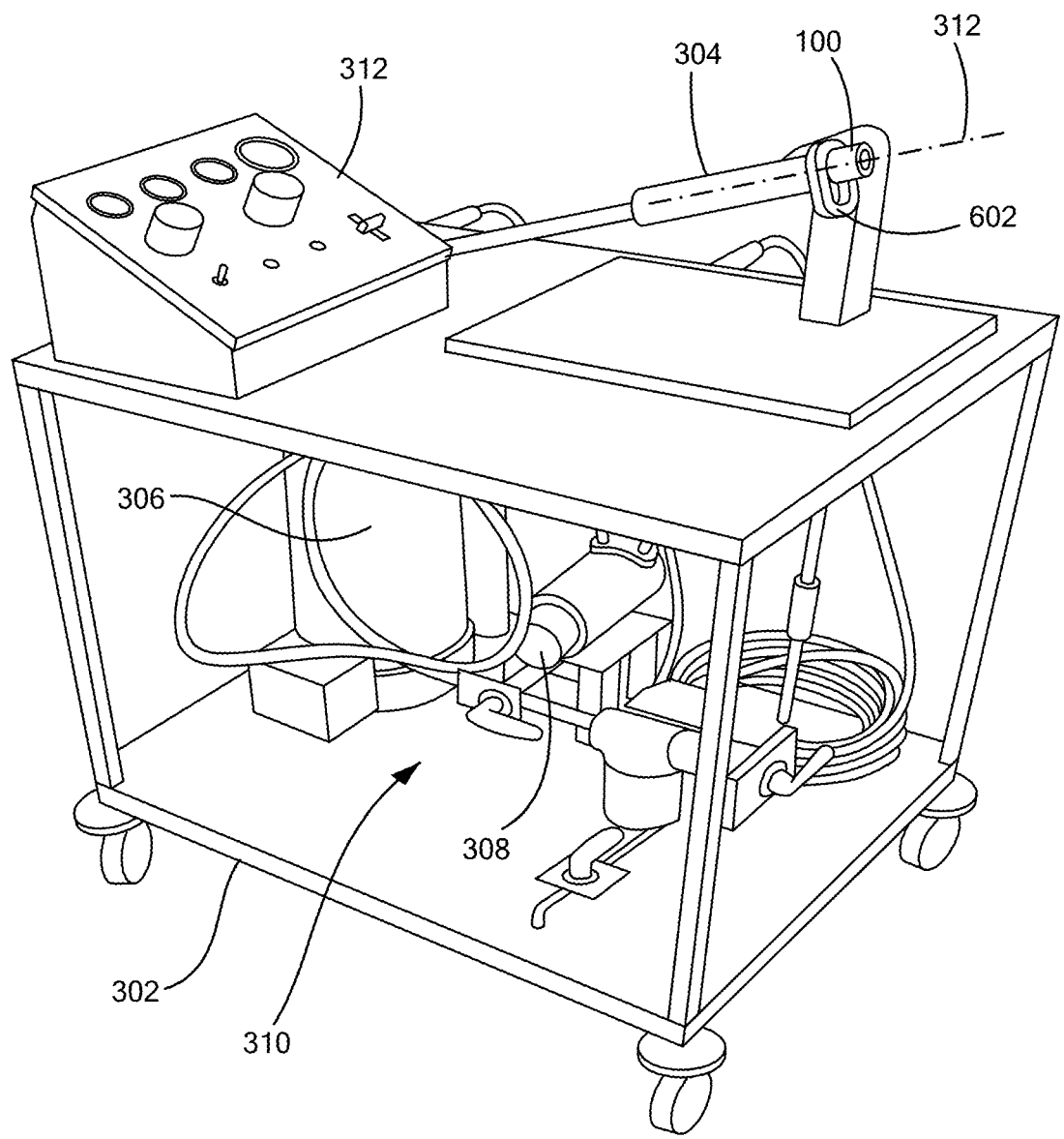
FIG. 3 is a perspective view of a cleaning system for a diaphragm pump, such as the exemplary single-port diaphragm pump of FIGS. 1 and 2, according to an embodiment of the present invention.

FIG. 3 is a perspective view of a cleaning system 300 for a diaphragm pump, such as the exemplary Symphony device 100. An exemplary single-port diaphragm pump 100 is shown attached to the cleaning system 300 for cleaning by the system 300. The system 300 may be mounted on a mobile cart 302. However, in other embodiments, the system 300 may be bench mounted, cabinet mounted, etc. The system 300 may be mobile, portable, stationary or fixed-in-place.

The system 300 includes a first coupler 304 that is configured to releasably mate with the input-output port 108 of the single-port diaphragm pump 100. The system 300 also includes a tank 306 configured to store a suitable cleaning fluid, a circulation pump 308 and a cleaning fluid circulation circuit (generally indicated at 310).

Figure 4:
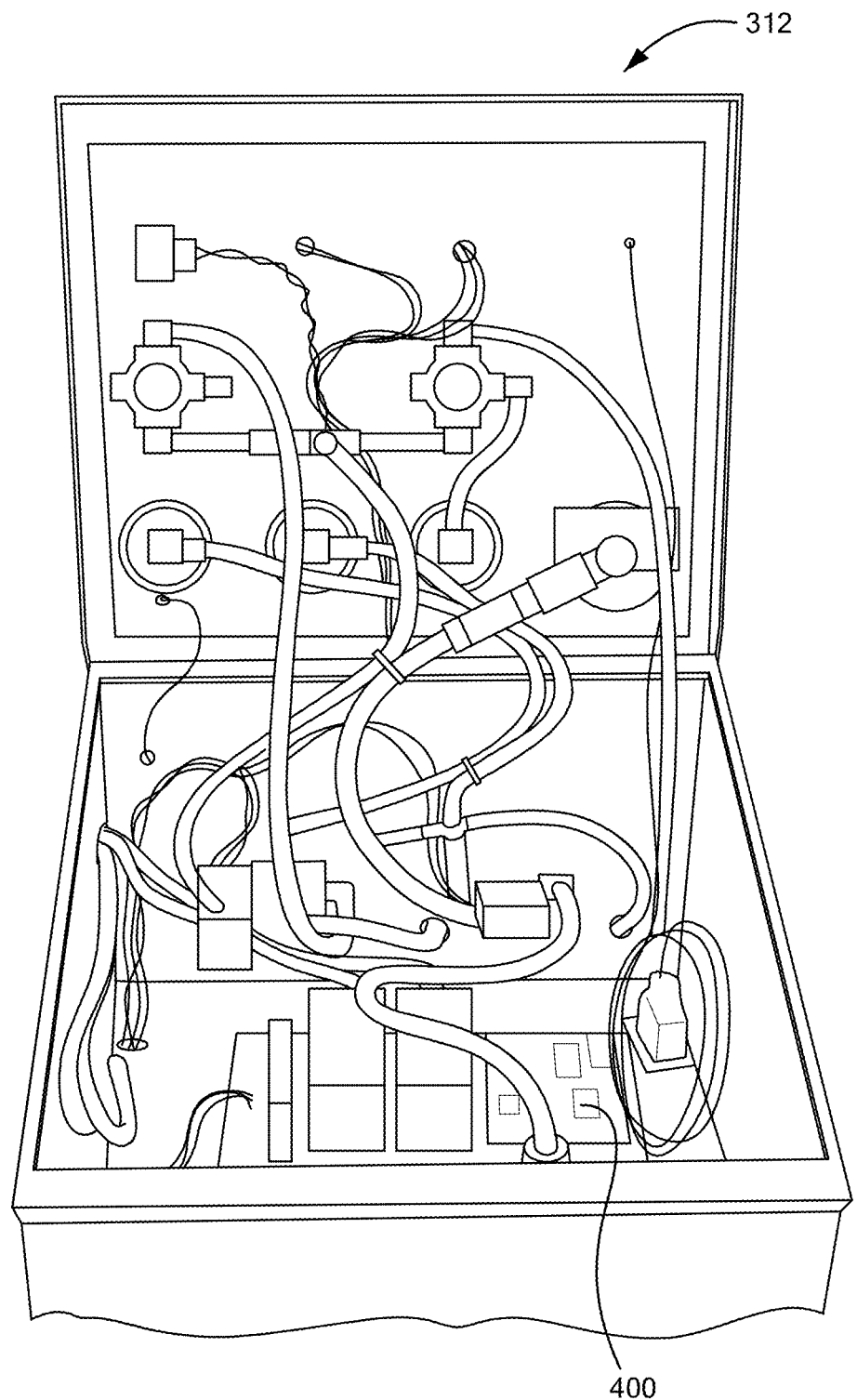
FIG. 4 is a perspective view of an interior of a control box/console of the cleaning system of FIG. 3.

The cleaning fluid circulation circuit 310 may include various valves, pressure/vacuum gauges, etc., some or all of which may be disposed in or on a control box/console 312 that provides a user interface to the system 300. FIG. 4 is a perspective view of an interior of the control box/console 312.

The control box/console 312 may also house a controller 400 that automatically measures pressures, vacuums, flow rates, user inputs via switches, dials, etc. The controller 400 may also monitor other parameters of the cleaning fluid circulation circuit 310 and control operation of some or all of the valves, etc. and/or display information via a suitable display screen, panel lights, annunciators, etc. The controller 400 may include a processor that executes instructions stored in a memory to perform these and other operations described herein.

Figure 5:
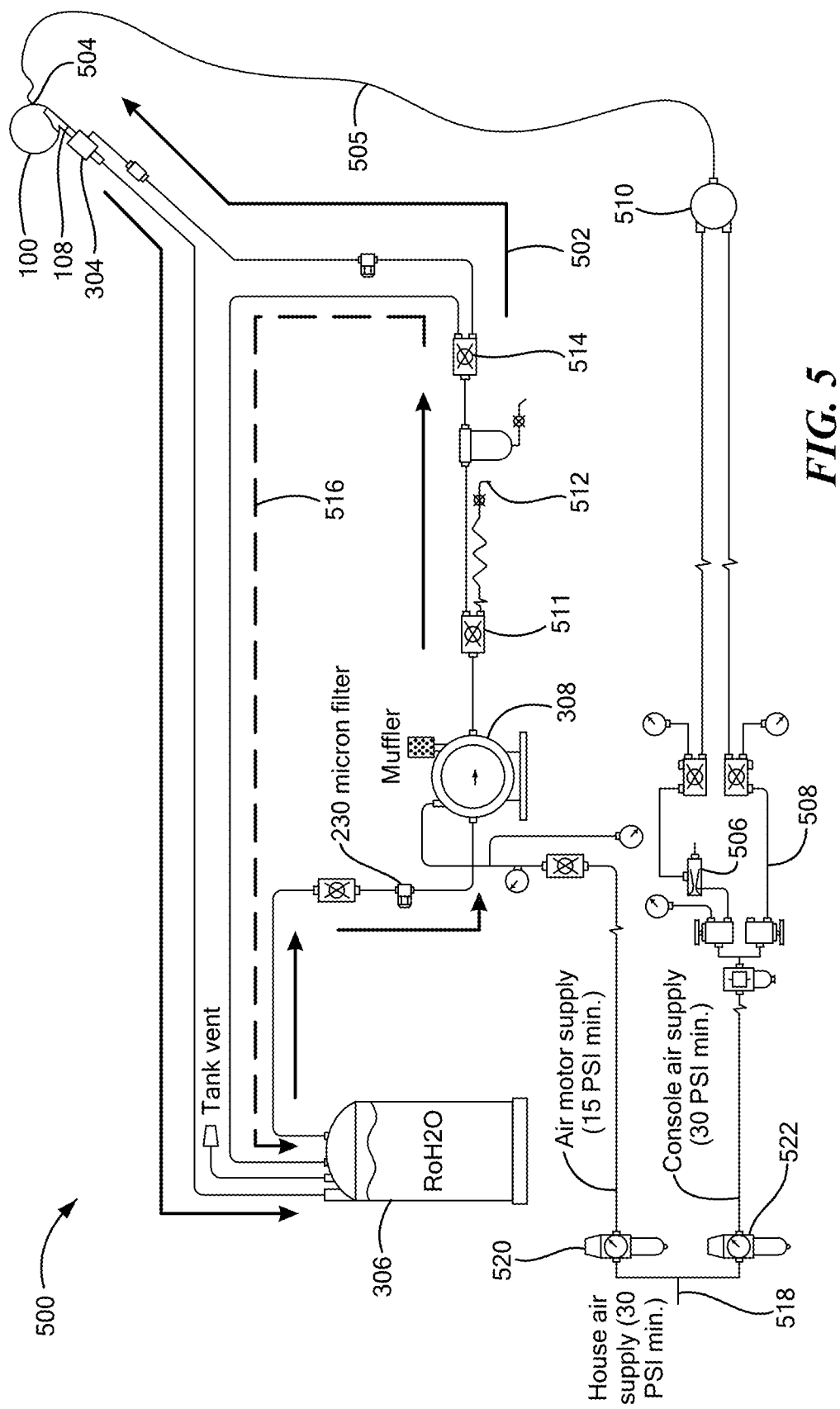
FIG. 5 is a schematic plumbing diagram of the cleaning system of FIG. 3.
Figure 6:
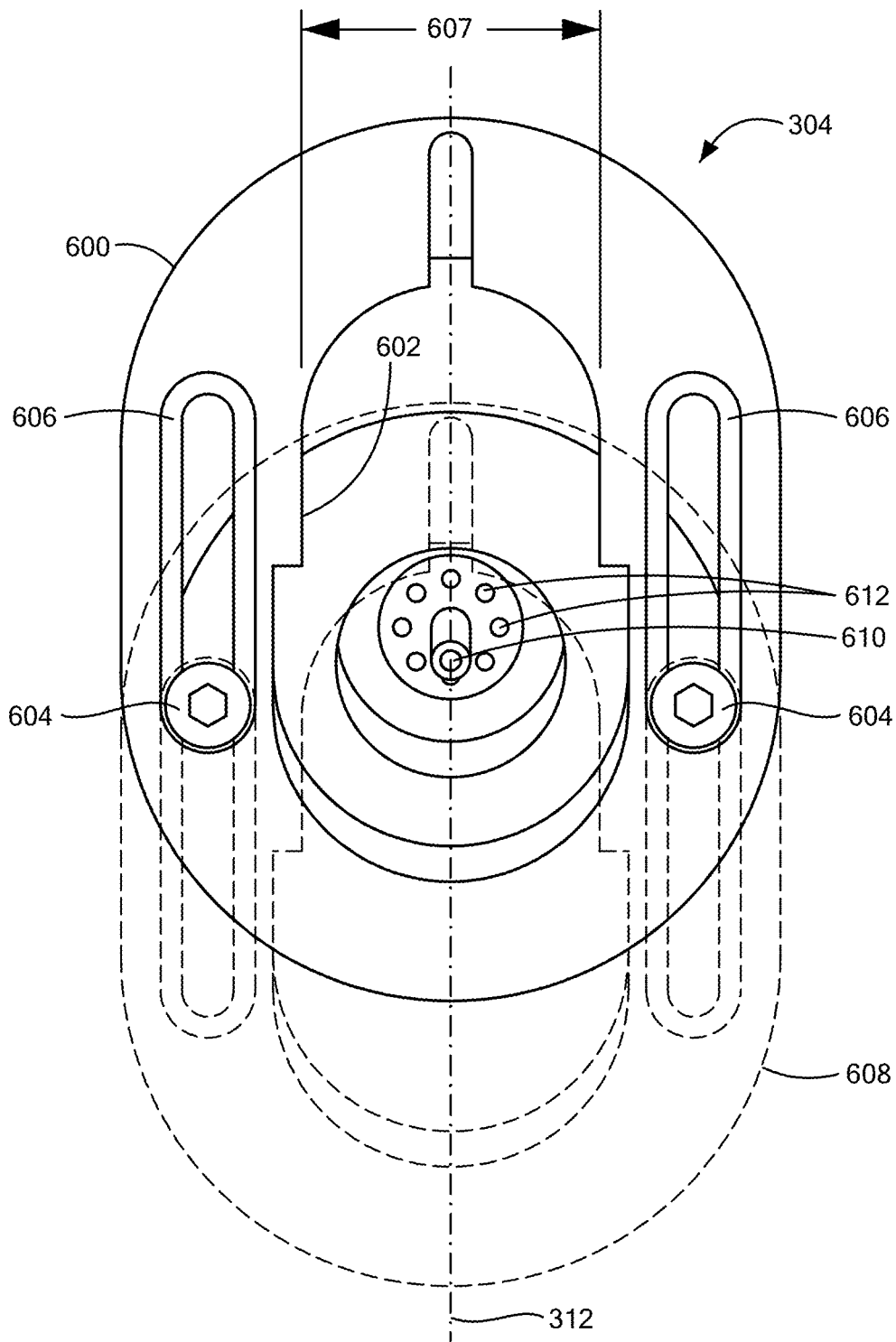
FIG. 6 is a front perspective view of a business end of a first coupler of the cleaning system of FIG. 3, which is configured to releasable mate, and thereby create a fluid-tight connection, with an input/output port of a diaphragm pump, such as the exemplary single-port diaphragm pump of FIGS. 1 and 2, according to an embodiment of the present invention.

FIG. 5 is a schematic plumbing diagram 500 of the cleaning system 300. As noted, the cleaning system 300 includes a first coupler 304 that is configured to releasably mate with the input-output port 108 of the diaphragm pump 100. When mated with the input-output port 108, the first coupler 304 forms a fluid-tight connection with the input-output port 108. FIG. 6 is a front perspective view of a business end of the first coupler 304.

The first coupler 304 may include a latch 600 configured to releasably lock the input-output port 108 to the first coupler 304. As noted, the input-output port 108 may include a flange, thread or other connection feature 111 for firmly or rigidly connecting the conduit 109 to the input-output port 108.

In the embodiment shown in FIG. 6, the latch 600 is in the form of a yoke 602 slideably attached to the first coupler 304 by two screws 604. Slots 606 in the latch 600 permit the yoke 602 to translate vertically between two positions defined by vertically separated ends of the slots 606. In one position, as shown in solid line in FIG. 6, the yoke 602 permits the input-output port 108 to enter the latch 600 and mate with the first coupler 304.

A portion 607 of the opening defined by the yoke 602 is narrower than a remaining portion of the opening defined by the yoke 602. In the second position 608, shown in FIG. 3 and in dashed line in FIG. 6, the portion 607 of the yoke 602 mechanically captures the feature 111 of the input-output port 108 and presses it against the first coupler 304 to form a fluid-tight connection between the input-output port 108 and the first coupler 304. After the diaphragm pump 100 has been cleaned, the yoke 602 can be returned to the first position, thereby freeing the feature 111, and the input-output port 108 may be withdrawn from the latch 600 and, thereby, detached from the first coupler 304.

Figure 7:
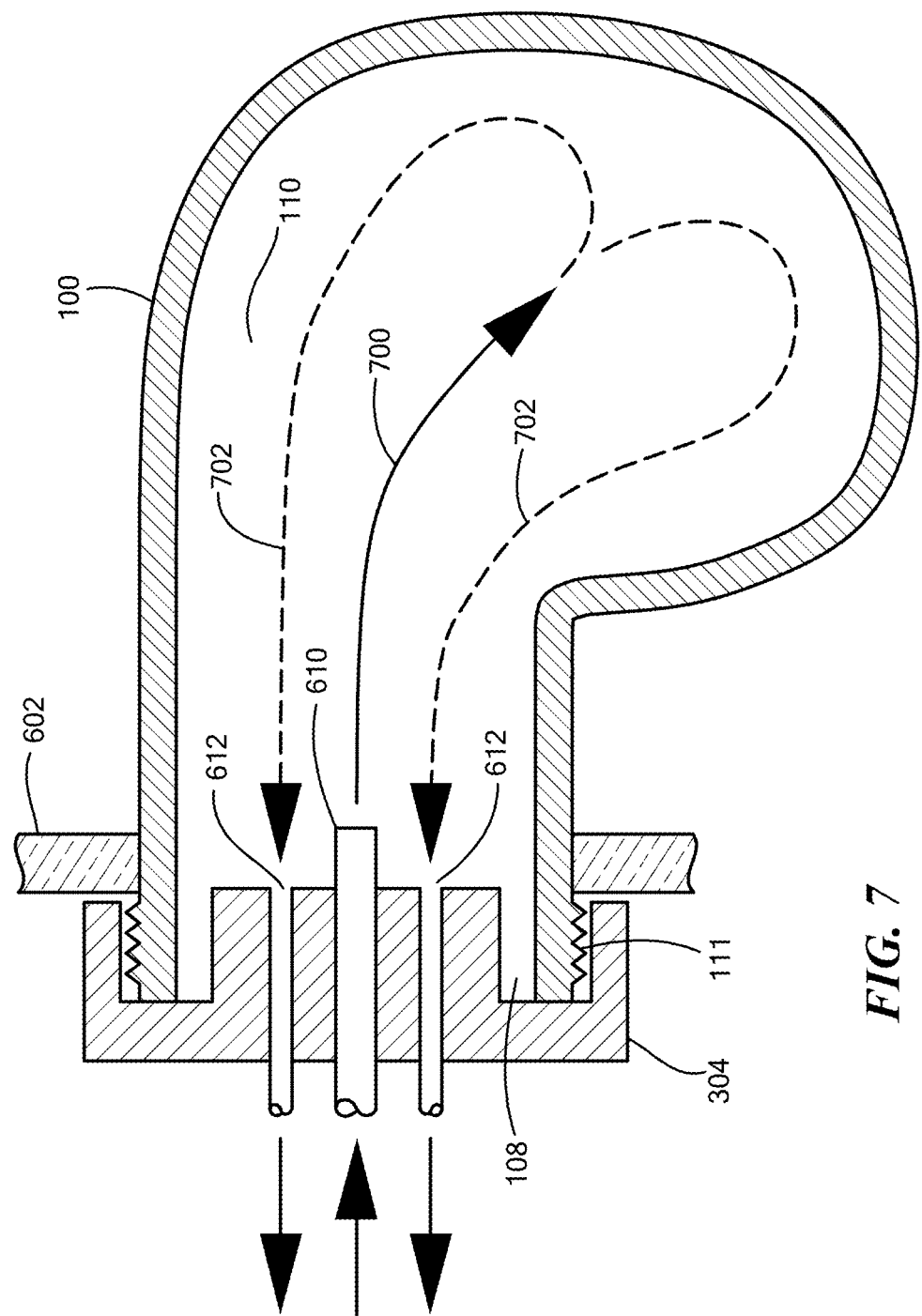
FIG. 7 is a cross-sectional view of a portion of the first coupler of FIG. 6, with the exemplary single-port diaphragm pump of FIGS. 1 and 2 attached thereto, illustrating an exemplary flow pattern of cleaning fluid injected into, and simultaneously removed from, the single-port diaphragm pump by the first coupler, according to an embodiment of the present invention.

As can be most clearly seen in FIGS. 6 and 7, the first coupler 304 includes an injector nozzle 610. The injector nozzle 610 is configured and aimed to inject a cleaning fluid 700 into the interior 110 of the diaphragm pump 100. The first coupler 304 also includes a return port 612 that is also in fluid communication with the interior 110 of the diaphragm pump 100, when the first connector 304 is mated with the input-output port 108. In the embodiment shown in FIG. 6, the return port 612 includes a plurality of apertures arranged in a circle.

Two such apertures 612 are called out in FIGS. 6 and 7. However, any number of apertures 612 may be used, and if more than one aperture 612 is used, the apertures 612 may be disposed in any arrangement. The arrangement may, but need not, encircle the injector nozzle 610. The injector nozzle 610 may, but need not, be coaxial with the return port 612 arrangement. The collective cross-sectional area of the apertures 612 (as measured transverse to the longitudinal axis 312 of the first coupler 304) can, but need not, be equal to, or exceed, the cross-sectional area of the injector nozzle 610.

As shown in FIG. 7, fresh cleaning fluid 700 can be injected into the interior 108 of the diaphragm pump 100 by the injector nozzle 610, and simultaneously soiled fluid can be removed from the interior 108 by the return port 612.

Figure 8:
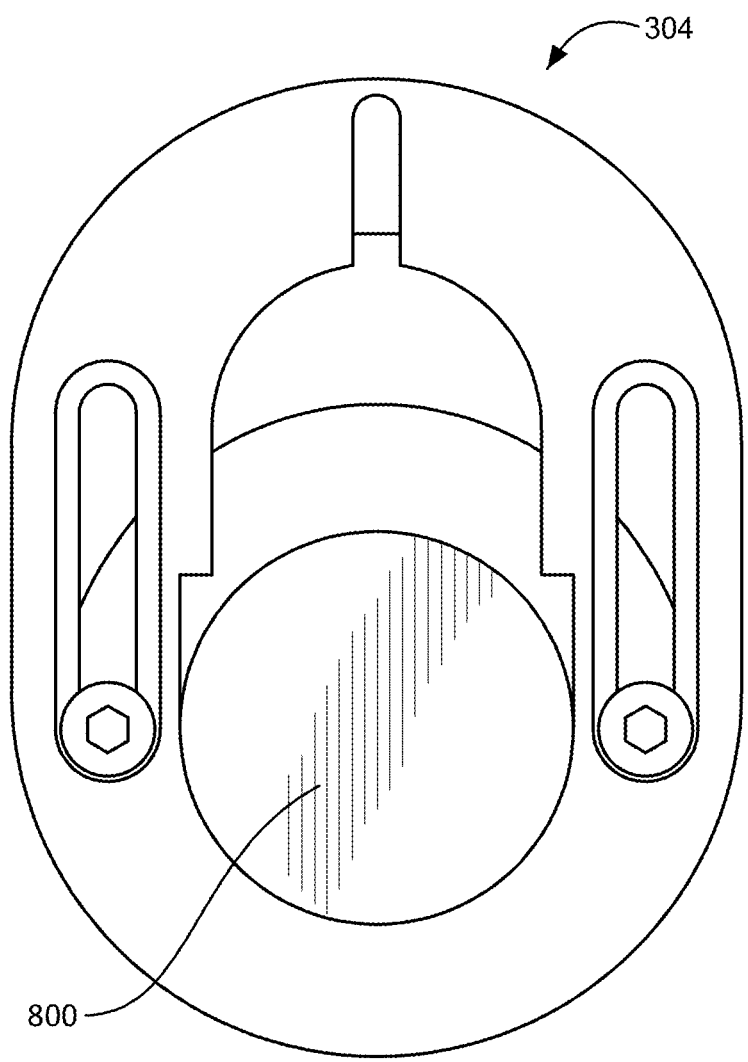
FIG. 8 is a front view of the business end of the first coupler of FIG. 6, with a protective plug installed to prevent contamination of the first coupler when not in use, according to an embodiment of the present invention.

FIG. 8 is a front view of the business end of the first coupler 304, with a protective plug 800 installed to prevent contamination of the first coupler 304 when not in use.

Returning to the schematic plumbing diagram 500 (FIG. 5) of the cleaning system 300, the tank 306 stores the cleaning fluid. The circulating pump 308 draws the cleaning fluid from the tank 306 and delivers the cleaning fluid under pressure to the injector nozzle 610, which directs a high-pressure stream of the cleaning fluid 700 (FIG. 7) into the interior 110 of the diaphragm pump 100. The used cleaning fluid 702 exits the diaphragm pump 100 via the exit port 612 and returns to the tank 306, completing a cleaning fluid circuit, as generally indicated by a series of solid-line arrows 502 (FIG. 5). Suitable filters, valves, pressure regulators and access ports/vents are disposed along the cleaning fluid circuit 502.

During cleaning, the diaphragm 104 (FIG. 1) may be alternately driven between two positions, much the way the diaphragm 104 would be driven when the diaphragm pump 100 operates normally. This action by the diaphragm 104 agitates the cleaning fluid 700, enhancing cleaning efficiency. As noted, the diaphragm pump 100 includes a pneumatic actuation port 114. During cleaning, the pneumatic diaphragm activation port 114 may be coupled via a second releasable coupler 504 (FIG. 5) to an alternating source of gas pressure 505.

The alternating source of gas pressure 505 may include a Venturi vacuum generator 506 (for simplicity referred to herein as a "Venturi") configured to generate a relative partial vacuum (referred to herein as a "relative vacuum") and a source 508 of compressed gas. A toggle valve 510 couples the relative vacuum and the compressed gas to the pneumatic diaphragm activation port 114 of the diaphragm pump 100. The toggle value 510 alternates between supplying the relative vacuum and the compressed gas to the pneumatic diaphragm activation port 114 at a frequency between about 0.1 Hz and about 10 Hz.

The toggle valve 510 may, for example, be controlled by the controller 400 (FIG. 4), in coordination with supply of the cleaning fluid. The relative vacuum and the compressed gas should differ in pressure sufficiently to drive the diaphragm 104 through most or all of its design travel. In some embodiments, the relative vacuum has a pressure less than ambient atmospheric pressure, and the compressed gas has a pressure greater than ambient atmospheric pressure.

Depending on the type of circulation pump 308 used, the cleaning fluid circuit 502 may include a two-way valve 511 and a purge port 512 downstream of the circulation pump 308. A syringe (not shown) may be inserted in the purge port 512 and used to create a partial vacuum to draw cleaning fluid from the tank 306, into the circulating pump 308, to purge the circulating pump 308 of air.

The cleaning fluid circuit 502 may include a two-way valve 514. In one position, the two-way valve 514 directs the cleaning fluid from the circulating pump 308 to the injector nozzle 610, as described above. In the other position, the two-way valve 514 bypasses the first coupler 304 and directs the cleaning solution back to the tank 306, as indicated by dashed arrow 516, to flush at least a portion of the cleaning fluid circuit 502 of air and contaminants.

An external supply 518 of compressed gas, such as air, may be used to drive the circulation pump 308 and the Venturi 506 and to supply the source 508 of compressed gas. However, the gas supply 518 should be separated, such as by separate pressure regulators 520 and 522, to prevent compressor or motor oil fume contaminating the diaphragm 104. Alternatively, the circulation pump 308 may be electrically operated.

Pneumatic pressure in the source 508 of compressed gas should be in a range of about 6-8 PSI (41,368.5-55,158.1 Pa) to adequately reciprocate the diaphragm 104 in a Symphony device 100. For other single-port fluidic devices 100, an appropriate pneumatic pressure range for the source 508 of compressed gas may be determined empirically or theoretically, such as based on mechanical characteristics of the single-port fluidic device 100.

The relative partial vacuum generated by the Venturi 506 should be set in a range of about 2-3 inHg (6,772.78-10, 159.2 Pa) to adequately reciprocate the diaphragm 104 in a Symphony device 100. For other single-port fluidic devices 100, an appropriate partial vacuum may be determined empirically or theoretically, such as based on mechanical characteristics of the single-port fluidic device 100.

The cleaning system 300 is suitable for any single-port pump 100. The cleaning system 300 may automatically drive the diaphragm 104, thereby agitating the cleaning fluid 700, whereas manual methods for cleaning single-port pumps 100 do not drive the diaphragm 104. The cleaning system 300 simultaneously: (a) injects, under pressure, cleaning fluid 700 into the interior 110 of the diaphragm pump 100 and (b) withdraws used cleaning fluid 702 from the interior 110. Thus, the cleaning fluid 702 inside the diaphragm pump 100 is continuously replaced with clean fluid 7-2. Used cleaning fluid 702 is almost immediately expelled from the interior 110 of the diaphragm pump 100, so it cannot re-deposit contaminants on the interior of the diaphragm pump. Any contaminants left by the used cleaning fluid 702 are flushed out by the fresh cleaning fluid 700.

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Although aspects of embodiments may be described with reference to flowcharts and/or block diagrams, functions, operations, decisions, etc. of all or a portion of each block, or a combination of blocks, may be combined, separated into separate operations or performed in other orders. References to a "module" are for convenience and not intended to limit its implementation. All or a portion of each block, module or combination thereof may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

The controller 400, or portions thereof, may be implemented by one or more processors executing, or controlled by, instructions stored in a memory. Each processor may be a general purpose processor, such as a central processing unit (CPU), a graphic processing unit (GPU), digital signal processor (DSP), a special purpose processor, etc., as appropriate, or combination thereof.

The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective couplers, switch positions, interior volumes, valves, outputs, etc. and from one another and are not intended to indicate any particular order or total number of couplers, switch positions, interior volumes, valves, outputs, etc. in any particular embodiment. Thus, for example, a given embodiment may include only a second valve and a third valve.

What is claimed is:

1. A cleaning system for a diaphragm pump, wherein the diaphragm pump comprises a housing, a diaphragm disposed within the housing, and an input-output port, wherein the diaphragm and at least a portion of the housing collectively define a pump chamber interior, wherein the input-output port is in fluid communication with the pump chamber interior, and wherein the cleaning system comprises:
    (1) a tank configured to store a cleaning fluid;
    (2) a first coupler configured to releasably mate, and thereby create a fluid-tight connection, with the input-output port, wherein the first coupler comprises:
        (a) an injector nozzle having an input end and an output end, wherein the injector nozzle is configured such that, while the first coupler is mated with the input-output port, the injector nozzle is in fluid communication with, and oriented to direct a fluid stream toward, the pump chamber interior; and
        (b) a return port proximate, and distinct from, the output end of the injector nozzle and configured, such that while the first coupler is mated with the input-output port, the return port is in fluid communication with the pump chamber interior, wherein the injector nozzle is configured to direct the stream into the pump chamber interior simultaneous with the return port draining the pump chamber interior;
    (3) a circulation pump having an input and an output; and
    (4) a cleaning fluid circulation circuit in fluid communication with the tank, the input and the output of the circulation pump, the input end of the injector nozzle, and the return port, wherein the cleaning fluid circulation circuit is configured to deliver pressurized cleaning fluid from the tank to the injector nozzle and to return used cleaning fluid from the return port to the tank, and wherein the cleaning fluid circulation circuit comprises:
- (a) a first two-way valve having an input, a first output, and a second output, wherein the first two-way valve is user settable to either of two states and is configured to place the input into fluid communication with either the first output or the second output depending on the state of the first two-way valve, wherein the input is coupled to the output of the circulation pump, wherein the first output is coupled to the input end of the injector nozzle, and wherein the second output is coupled to the tank, thereby bypassing the first coupler;
- (b) a purge port; and
- (c) a second two-way valve having an input, a first output, and a second output, wherein the second two-way valve is user settable to either of two states and is configured to place the input of the second two-way valve into fluid communication with either the first output of the second two-way valve or the second output of the second two-way valve depending on the state of the second two-way valve, wherein the input of the second two-way valve is coupled to the output of the circulation pump, wherein the first output of the second two-way valve is coupled to the input of the first two-way valve, and wherein the second output of the second two-way valve is coupled to the purge port.

2. A cleaning system according to claim 1, wherein the circulation pump is pneumatically driven.

3. A cleaning system according to claim 1, wherein the circulation pump is electrically driven.

4. A cleaning system according to claim 1, wherein the diaphragm pump further comprises a pneumatic diaphragm activation port, and wherein the cleaning system further comprises:
- a second coupler configured to releasably mate with, and thereby create a gas-tight connection with, the pneumatic diaphragm activation port; and
- a source of gas configured to supply gas to the second coupler at a pressure that alternates, at a frequency between about 0.1 Hz and about 10 Hz, between a first pressure and a second pressure, wherein the second pressure is greater than the first pressure by at least about 1.45 PSI (9,997 Pa).

5. A cleaning system according to claim 4, wherein the source of gas comprises:
- a pneumatically driven Venturi configured to supply gas at about 2-3 inHg (6,772.78-10,159.2 Pa).

6. A cleaning system according to claim 4, wherein the first pressure is less than ambient atmospheric pressure, and the second pressure is greater than ambient atmospheric pressure.

7. A cleaning system according to claim 1, wherein the return port comprises a plurality of apertures arranged around the injector nozzle.

8. A cleaning system according to claim 1, wherein the injector nozzle is coaxial with the return port.

9. A cleaning system for a diaphragm pump, wherein the diaphragm pump comprises a housing, a diaphragm disposed within the housing, an input-output port, and a pneumatic diaphragm activation port, wherein the diaphragm and at least a portion of the housing collectively define a pump chamber interior, wherein the input-output port is in fluid communication with the pump chamber interior, and wherein the cleaning system comprises:
- (1) a tank configured to store a cleaning fluid;
- (2) a first coupler configured to releasably mate, and thereby create a fluid-tight connection, with the input-output port, wherein the first coupler comprises:
  - (a) an injector nozzle having an input end and an output end, wherein the injector nozzle is configured such that, while the first coupler is mated with the input-output port, the injector nozzle is in fluid communication with, and oriented to direct a fluid stream toward, the pump chamber interior; and
  - (b) a return port proximate, and distinct from, the output end of the injector nozzle and configured, such that while the first coupler is mated with the input-output port, the return port is in fluid communication with the pump chamber interior, wherein the injector nozzle is configured to direct the stream into the pump chamber interior simultaneous with the return port draining the pump chamber interior;
- (3) a circulation pump having an input and an output;
- (4) a cleaning fluid circulation circuit in fluid communication with the tank, the input and the output of the circulation pump, the input end of the injector nozzle, and the return port, wherein the cleaning fluid circulation circuit is configured to deliver pressurized cleaning fluid from the tank to the injector nozzle and to return used cleaning fluid from the return port to the tank;
- (5) a second coupler configured to releasably mate with, and thereby create a gas-tight connection with, the pneumatic diaphragm activation port; and
- (6) a source of gas configured to supply gas to the second coupler at a pressure that alternates, at a frequency between about 0.1 Hz and about 10 Hz, between a first pressure and a second pressure, wherein the second pressure is greater than the first pressure by at least about 1.45 PSI (9,997 Pa), and wherein the source of gas comprises a pneumatically driven Venturi configured to supply gas at about 2-3 inHg (6,772.78-10,159.2 Pa).

10. A cleaning system according to claim 9, further comprising a first two-way valve in the cleaning fluid circulation circuit, wherein the first two-way valve has an input, a first output, and a second output, wherein the first two-way valve is user settable to either of two states and is configured to place the input into fluid communication with either the first output or the second output depending on the state of the first two-way valve, wherein the input is coupled to the output of the circulation pump, wherein the first output is coupled to the input end of the injector nozzle, and wherein the second output is coupled to the tank, thereby bypassing the first coupler.

11. A cleaning system according to claim 10, further comprising a purge port and a second two-way valve in the cleaning fluid circulation circuit, wherein the second two-way valve has an input, a first output, and a second output, wherein the second two-way valve is user settable to either of two states and is configured to place the input of the second two-way valve into fluid communication with either the first output of the second two-way valve or the second output of the second two-way valve depending on the state of the second two-way valve, wherein the input of the second two-way valve is coupled to the output of the circulation pump, wherein the first output of the second two-way valve is coupled to the input of the first two-way valve, and wherein the second output of the second two-way valve is coupled to the purge port.

12. A cleaning system according to claim 9, wherein the circulation pump is pneumatically driven.

13. A cleaning system according to claim 9, wherein the circulation pump is electrically driven.

14. A cleaning system according to claim 9, wherein the first pressure is less than ambient atmospheric pressure, and the second pressure is greater than ambient atmospheric pressure.

15. A cleaning system according to claim 9, wherein the return port comprises a plurality of apertures arranged around the injector nozzle.

16. A cleaning system according to claim 9, wherein the injector nozzle is coaxial with the return port.

* * * * *

UNITED STATES PATENT AND TRADEMARK OFFICE
CERTIFICATE OF CORRECTION

Page 1 of 1

PATENT NO. : 12,145,181 B2
APPLICATION NO. : 17/060329
DATED : November 19, 2024
INVENTOR(S) : Emmanuel N. Ilongo It is certified that error appears in the above-identified patent and that said Letters Patent is hereby corrected as shown below:

In the Specification

Column 5, Line 67:
Now reads: "108"; should read -- 110 --

Column 6, Line 2:
Now reads: "108"; should read -- 110 --

Signed and Sealed this
Eleventh Day of February, 2025

Coke Morgan Stewart
*Acting Director of the United States Patent and Trademark Office*